United States Patent [19]

Bader

[11] Patent Number: 4,934,999
[45] Date of Patent: Jun. 19, 1990

[54] CLOSURE FOR A MALE URETHRA

[76] Inventor: Paul Bader, Strutweg 1, 7070 Schwabisch Gmund-7, Fed. Rep. of Germany

[21] Appl. No.: 225,172

[22] Filed: Jul. 28, 1988

[30] Foreign Application Priority Data

Jul. 28, 1987 [DE] Fed. Rep. of Germany ....... 3724875
Jun. 27, 1988 [DE] Fed. Rep. of Germany ....... 3821631

[51] Int. Cl.⁵ ............................................. A61M 29/02
[52] U.S. Cl. ........................................ 600/29; 600/31; 606/192; 128/DIG. 25; 623/12
[58] Field of Search ................... 600/29, 32, 327, 328; 128/341, 344, D, 25, 79 A, 899; 604/96, 104; 623/12

[56] References Cited

U.S. PATENT DOCUMENTS

| | | | |
|---|---|---|---|
| 3,216,420 | 11/1965 | Smith et al. | 604/328 |
| 3,797,478 | 3/1974 | Walsh et al. | 600/29 |
| 3,812,841 | 5/1974 | Isaacson | 128/D25 |
| 4,183,358 | 1/1980 | Cohen | 604/328 |
| 4,555,242 | 11/1985 | Saudagar | 604/96 |
| 4,643,169 | 2/1987 | Koss et al. | 128/D25 |
| 4,666,428 | 5/1987 | Mattioli et al. | 128/79 A |
| 4,686,962 | 8/1987 | Haber | 600/30 |
| 4,781,176 | 11/1988 | Ravo | 600/30 |

FOREIGN PATENT DOCUMENTS 602099 of 1934 Fed. Rep. of Germany .
1566405 of 1971 Fed. Rep. of Germany .
1957693 of 1971 Fed. Rep. of Germany .

Primary Examiner—Dalton L. Truluck
Assistant Examiner—Denise W. DeFranco
Attorney, Agent, or Firm—Nixon & Vanderhye

[57] ABSTRACT

A closure device for a male urethra, which is formed by an elongated valve device to be inserted into the urethra and to be releasably fastened therein. The elongated object may be formed by a single basic body element, or by a basic body element combined with at least one intermediate element and an end element. The valve is open at both ends and includes a longitudinal through hole. The valve body, at least on its front end, includes a removable closure plug. The valve body is partly enclosed by a double-membrane tube that can be pressurized and expanded to secure the device within the urethra. The basic body element of the valve body is provided with at least one radial hole to permit the introduction of fluid such as air into a space between an inner and outer membrane which comprise the double membrane tube or sleeve. An opening provided in the inner sleeve is offset relative to the radial opening in the valve body. In this way, after air or other fluid is supplied to the space between the membranes, the inner membrane will seal the radial opening in the valve body. A hand pump is provided to supply as well as release air from the valve body.

22 Claims, 2 Drawing Sheets

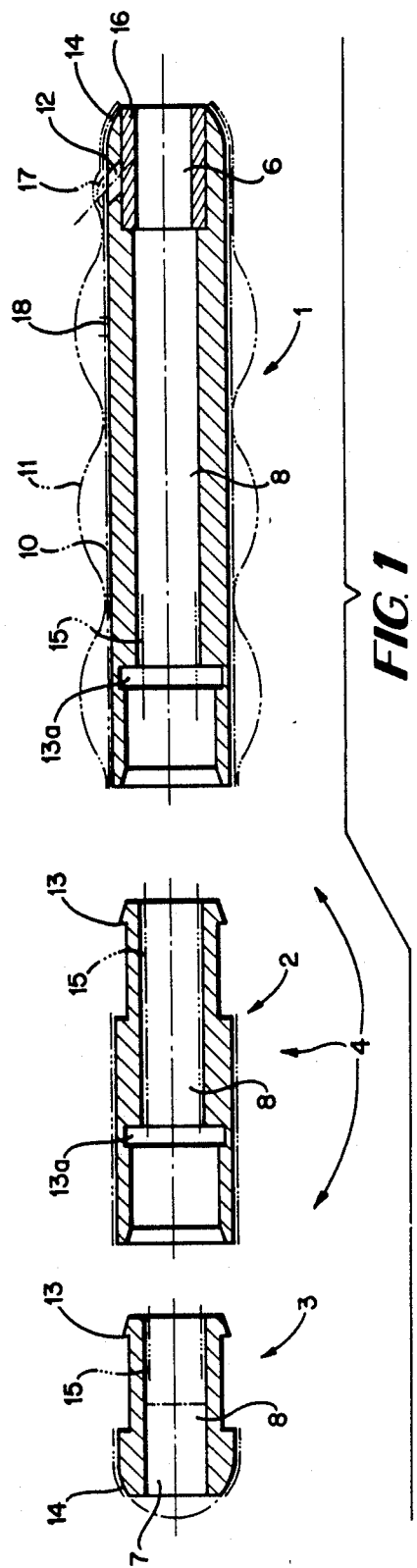
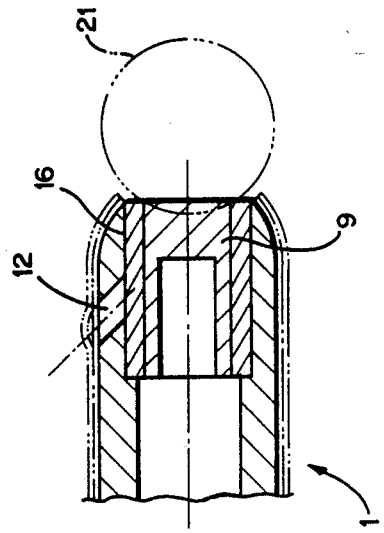
FIG. 1
FIG. 2

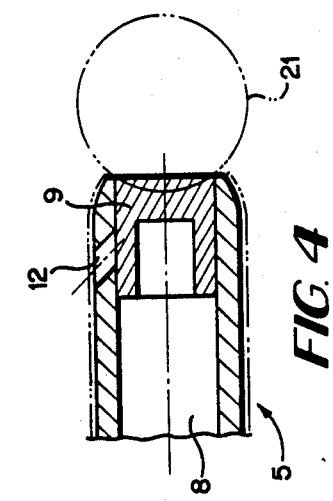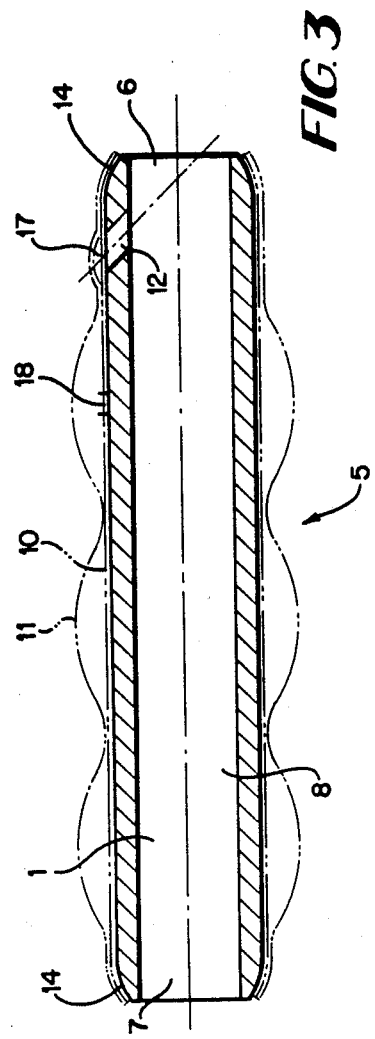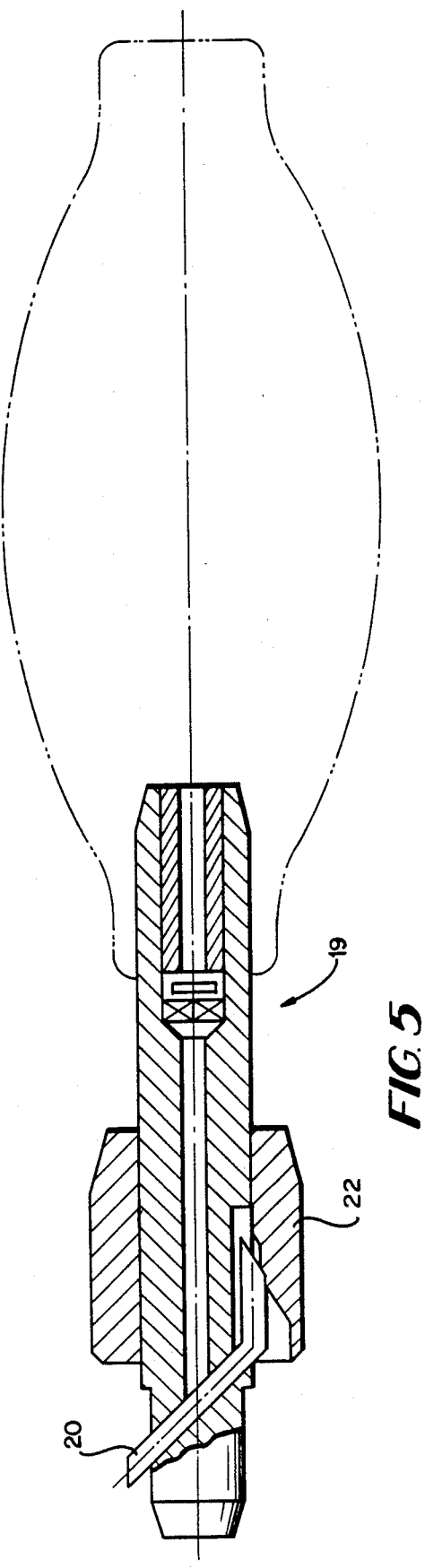

CLOSURE FOR A MALE URETHRA

BACKGROUND AND SUMMARY OF THE INVENTION

This invention relates to a closure for a male urethra, and specifically, to a closure formed by an elongated device which is inserted in the urethra and temporarily fastened therein.

Closure of the male urethra may be necessary for various reasons. One such reason is to protect the bed from bedwetting or nocturnal pollution. Another reason is to prevent the discharge of sperm during sexual intercourse, i.e., as a means of birth control.

One device for safe family planning is disclosed in the German patent application No. DE-051,566,405. The device includes a short, slender tube, constructed of very extensible soft rubber, to be inserted into the male urethra. The tube can be closed at one end, and connected at the other end in airtight and watertight relationship to the neck part of a filling tube that constitutes an extension of a valve head. Water or air is forced into the tube by a syringe or an inflation bellows, so that the tube expands and is thereby held in the urethra.

Another device for family planning is proposed in German patent application DE-OS No. 1,957,693. This device includes a number of spreader arms placed in a short, slender, extensible soft rubber tube or the like, which is introduced into the male urethra. The tube is solidly connected at its open end to a neck section of the device. Turning a screw in a head section of the device spreads the spreader arms apart so that the tube is stretched to such an extent that its most severely stretched end rests tightly against the inner edge of the neck of the glans penis to produce a completely tight closure of the urethra, and at the same time provide a firm hold therein.

According to the statements of the inventor (a physician) of both inventions cited above, the anatomic conditions of the male are virtually ideal for applying a contraceptive. Nevertheless, with the exception of the condom, "the bulk of the usual contraceptive measures" are carried out in the body of the woman.

It has been found that the device proposed in DE-OS No. 1,957,693 has a critical drawback in that it does not create a tight fit, and therefore, seminal fluid can escape between the urethra wall and the closure. When the tube is stretched by means of the small number of spreader arms, a polygon is formed. Because of this, two parallel but spaced surfaces are formed between contact points so that an effective seal cannot be formed, absent infinitely large tensile forces stretching the parallel surfaces.

However, the important drawbacks that both of the above inventions have in common are the fact that the valve head protruding from the penis has an annoying and discomforting effect in every respect, both in wearing the device and/or in performing sexual intercourse. Moreover, the device must be removed from the urethra for urinating, and then has to be reinserted if this device is worn by incontinent persons, or if used as a contraceptive device.

The object of this invention is to provide an improved device which is economical to manufacture, and which can be placed in the male urethra so as to be absolutely liquid-tight, which seals off on a relatively large surface area around the outside of the device, and which need not be removed from the urethra for urinating.

Another object is to provide a device which produces little or no discomfort after a short acclimation phase, with insertion and removal being easy to accomplish at anytime without difficulty.

Another purpose of this invention is to design a closure by which a penis may be artificially kept erect.

In general terms, this invention achieves the above objects by providing an elongated open-ended device having, in one embodiment, a basic body element, at least one intermediate element, and an end element, thus forming a multi-element cylindrical valve body, each having substantially identical outside and inside diameters, and with a longitudinal hole or bore formed through each of the elements. Alternatively, the device may be of single element design, comprising essentially only the basic body element.

The valve body is partly enclosed by a double-membrane tube arrangement wherein fluid under pressure is introduced between inner and outer membranes, causing the outer membrane to expand against the urethra. The fluid may be introduced through the longitudinal bore, through a radial hole formed in the valve body, and through an air passage formed in the inner membrane. When pressurized, the double-membrane tube keeps the valve body absolutely leakproof and immovable within the urethra upon expansion of the outer membrane.

The valve body is also provided, at least on its front end, with a removable closure plug. When installed in the valve body, the removable closure plug closes the valve body and creates an airtight and liquid-tight seal, so that it is absolutely effective against bedwetting and/or discharge of sperm.

The cylindrical valve body can be inserted into the urethra easily and without complication. The wall of the cylindrical valve body rests against the wall of the urethra uniformly over its entire outer surface. Thus, the prerequisite for a good full-area seal is created.

As noted above, the basic body element may be used with at least one intermediate element and the end element to form an extended multi-element valve body. By thus using a multi-element valve body there is achieved the further advantageous function of the device of providing means for enabling artificial erection of the penis. Further, in this regard, the basic body, the intermediate element(s) and the end element can be telescopically fitted into one another so that the connections are undetachable, but nevertheless flexible within limits. By such flexible connection of the individual valve elements, the elongated closure device can easily adapt to the natural curvature of the penis while being flexible enough not to cause any pain, especially during sexual intercourse.

As a result of the fact that all elements have substantially identical inside and outside diameters and because the forward and rearward ends of the device are rounded, insertion and removal of the device are relatively easily accomplished without any significant discomfort. In addition, there are no discharge difficulties while urinating.

In a further aspect of the invention, an internal coating may be applied to the interior surface of the longitudinal through bore of the multi-element valve body, in the area of the attachment sites of basic body, intermediate and end elements. The interior coating is flexible and can follow the movements of the elements without being damaged. The purpose of the interior coating is to provide a liquid-tight seal so that no urethral liquid can penetrate the attachment sites. As a result, no fungi can develop that could otherwise represent a source of infection.

In a further advantageous aspect of the invention, a cylindrical sleeve, open on both ends, is placed within an enlarged opening at the front end of the basic body element. This sleeve may then receive a slightly modified closure plug. It will be appreciated that the outside edge of the sleeve, and the outside area of the plug are flush with the front edge of the valve body so as to present a smooth external surface configuration. The sleeve is designed to close the radial hole formed in the area of the basic body for supplying and removing fluid from between the inner and outer membranes, so that no urine can enter the radial hole. The closure plug that is then pressed into the sleeve and is flush with the front edge of the valve body, while closing the inside longitudinal through bore in a liquid-tight manner so that no semen can escape during intercourse.

A fine cord or string is incorporated into the closure plug and projects in a preferably ring-shaped configuration from the plug. Thus, one is able to pull the plug from the sleeve (for urinating). The sleeve itself can easily be removed from the valve body with the help of a mini-discharge bolt.

One significant advantage of this invention relates to the fact that the closure plug has exactly the same outside diameter at its front end as at its rear end. As a result, the valve body can be inserted into the urethra, rearward end first, to the extent that the front end is actually placed behind the urethral orifice, so that no annoying part, e.g., a valve head, protrudes from the urethra. As stated above, removal of the closure from the urethra can take place either by pulling the fine cord, or the entire device may be pushed out of the urethra from behind, with the help of the fingers, by light pressure on the penis, pressing the valve body out of the urethra from behind.

The above-mentioned double-membrane tube or sleeve is defined by an inner jacket membrane and an outer membrane, secured at two ends by an inner jacket membrane and an outer membrane, secured at their ends by gluing or bonding, with the outer membrane designed for radial expansion in all or selected areas. Thus, the outer membrane can be constructed so as to fully expand radially and smoothly about is entire circumference, or selectively as in a bellows, or lamellar bellows. The inner jacket membrane can be supported on the valve body evenly, but in the area of the radial hole in the basic body element it can be provided with a reinforcing mushroom-shaped head and an adjacent air passage opening, as will be described further herein.

In stretched or expanded condition, the valve body is kept firmly in the urethra by the radially expanded outer membrane. At the same time, the reinforcing mushroom-shaped head on the inner membrane acts as check valve to prevent escape of fluid that has been brought into the space between the inner and outer membranes for securing the valve body in the urethra.

The gas or other pressure fluid may be pumped into the valve body and into the double membrane tube by an inflation pump valve which is adapted to extend into and through the radial opening provided in the valve body adjacent the front end of the valve body, so that the fluid is confined to flow through the air passage formed in the inner membrane and then into the space between the inner and outer membranes.

A longitudinal distance or offset between the radial hole in the valve body and the air passage opening in the inner membrane is required because the inner jacket membrane and the outer membrane are glued together approximately in the area of the glans penis, so that in this area the outer membrane cannot be allowed to expand since this would cause pain to the user.

In summary, with the removable closure plug in place, it will be appreciated that reliable protection from bedwetting and from nocturnal pollution is provided by the valve device of the present invention.

The invention is also eminently suitable as a contraceptive device. When conventional products for contraception are compared, the proposed invention has a number of substantial advantages. For example, the device of this invention has a very long service life when handled properly. Only the double membrane tube, and possibly the accompanying reinforcing mushroom-shaped head, require occasional replacement. The lifetime of the double membrane tube is likely to be approximately one year, while the valve body and closure plug should last approximately 5–10 years. Replacement of any or all parts should present no difficulties.

Viewed from the standpoint of hygiene there are no comparable devices known to be in existence at this time.

From an emotional standpoint, the proposed invention makes the man even more male, for which reason the lengthened form is also proposed as an alternative.

The proposed invention is also easily mass produced and therefore economical.

Further objects and advantages of the invention will become apparent from the detailed description which follows.

BRIEF DESCRIPTION OF THE DRAWINGS

FIG. 1 is an enlarged cross-sectional side view of the urethra closure device having a multi-element valve body in accordance with one exemplary embodiment of the invention, with individual sections separated;

FIG. 2 is a partial cross-sectional side view of the front end of the device shown in FIG. 1, and with a removable plug inserted therein;

FIG. 3 is an enlarged cross-sectional side view of a urethra closure device comprising a single element valve body in accordance with another exemplary embodiment of the invention;

FIG. 4 is a partial cross-sectional side view of the front end of the device shown in FIG. 3, but with an alternative removable plug inserted therein; and FIG. 5 is a is a cross-sectional side view of an inflation bellows and associated intake valve and plug in accordance with the invention.

DETAILED DESCRIPTION OF THE DRAWINGS

With reference to FIG. 1, a urethra closure device is illustrated which includes a valve body 4 comprising a basic body element 1, an intermediate element 2, and an end element 3. Each element is constructed in substantially hollow, cylindrical form, so that the device includes a the front opening 6 at one end, a rear opening 7 at the other end, and a longitudinal through bore 8 that connects front opening 6 with rear opening 7. At its front end, the multi-element valve body 4 is provided with a closure 9 in the form of a removable plug inserted in front opening 6 as best seen in FIG. 4, and as further explained below. Radially adjacent the closure plug 9, the basic body element 1 is also provided with a radially extending hole or aperture 12, for a purpose to be explained further herein.

The multi-element valve body 4 is at least partly enclosed by a double-membrane tube or sleeve formed by inner and outer membranes 10, 11, respectively which are telescopically received over the valve body. The inner membrane 10 encloses substantially the entire multi-element device, while outer membrane 11 is confined substantially to the basic body element 1.

In the multi-element valve body 4 illustrated in FIG. 1, the basic body element 1, intermediate element 2 and end element 3 are provided with mating attachment elements including tapered or conical bosses 13 which snap-fit into engagement with grooves 13a formed in elements 2, 1, respectively when the elements are assembled in telescoping relationship, one within the other. It will be understood that, at these attachment sites, the individual elements are movable relative to each other so as to allow the device to be conformable to the natural curvature of the penis. The basic body element 1, intermediate element 2, and end element 3 are also formed to have substantially identical internal and external diameters when the elements are assembled, and the multi-element valve body 4 is also provided with rounded ends 14 to facilitate insertion and removal of the device.

In addition, an internal coating 15 may be applied in the area of the interengaging attachment elements 13, 13a connecting basic body element 1 to intermediate element 2, and intermediate element 2 to end element 3 within the longitudinal through bore 8. This coating serves to seal the joints between the elements, preventing urethral liquid from penetrating into the attachment elements.

With reference to FIG. 1, an open-ended cylindrical sleeve 16 may be inserted within an enlarged counter-bore formed at the open end 6 of the basic body element 1. Thereafter, a smaller closure plug 9 than that used in the FIG. 4 embodiment may be placed within the sleeve as shown in FIG. 2. To the plug is attached a fine cord or string 21, shown in phantom in FIGS. 2 and 4.

Preferably, the outer edge of sleeve 16, the outside surface of closure plug 9, and the front edge of the valve body at opening 6 are flush, thereby presenting a smooth exterior surface which further facilitates insertion and removal of the device.

The sleeve-like double membrane tube is formed by suitable elastic, biocompatible materials, and includes an inner jacket membrane 10 and an outer membrane 11. The membranes are joined together at the forward and rearward edges of the outer membrane 11. Inner membrane 10 is expandable only within very narrow limits and tightly encloses substantially the entire valve body 4. In this regard, the inner jacket membrane 10 also covers the radial hole 12 formed in the body element 1. For reinforcement purposes, a reinforcing mushroom-shaped head 17 is provided on jacket membrane 10 in the area of radial hole 12 since the membrane is heavily stressed in this location by the mechanical plug, and by repeated expansion and deflation operations. An air outlet opening or passage 18 is provided in jacket membrane 10 in the proximate vicinity, but longitudinally spaced from the radial hole 12. An operative flow passage is thus established between the through bore 8, hole 12, passage 18 and the space between membranes 10 and 11.

Membrane 10 is preferably placed over substantially the entire valve body. In the forward area of basic body element 1 the extensible, inflatable part of outer membrane 11 commences about 3 cm behind the front edge of basic body element 1 and ends about at the rearward end of the basic body element, as best seen in FIG. 1. The ends of membrane 11 are secured to membrane 10 by any suitable means such as gluing, etc., to form the double membrane tube or sleeve structure.

With reference now to FIG. 3, another exemplary embodiment of the invention is illustrated which comprises a single element valve body 5. This embodiment is similar to the embodiment illustrated in FIG. 1, with the significant exception that intermediate element 2 and end element 3 are omitted. In other words, the single element valve body 5 comprises essentially only the substantially cylindrical basic body element 1.

As in the FIG. 1 embodiment, the single element valve body is provided at its forward end with a removable closure plug 9 inserted within the through bore 8. It will be appreciated that a combination sleeve 16 and closure 9 shown in FIGS. 1 and 2 may also be used in the FIG. 3 embodiment.

The single element valve body is also provided with a double membrane tube or sleeve 10, 11, a radial bore 12 and a mushroom-shaped head 17, and air passage 18, as in the FIG. 1 embodiment.

Placing the closure device as illustrated in FIGS. 1 or 3 in a male urethra is a relatively simple and painless operation. The single or multi-element valve body 4 or 5 is inserted into the urethra, until the basic body element 1 has substantially disappeared in the urethra. Air or other fluid is then supplied through front opening 6 and into the radial hole 12 by means of a small hand pump 19, which is inserted into the front opening 6. A plug 20 of the hand pump 19 may be moved upwardly into the radial hole 12 by a camming sleeve 21 in order to lightly raise the membranes 10, 11 adjacent the reinforcing mushroom-shaped head 17 thereby facilitating flow into the membrane tube to cause expansion of the outer membrane 11 with air or other fluid. During pumping, the air or other fluid flows through air passage opening 18 between the surface of basic body 1 and the outer skin of jacket membrane 10. The air or other fluid then inflates the outer membrane 11 so that it is pressed against the wall of the urethra to thus fasten the basic body element 1 of valve body 4 or 5 in the urethra. At the same time, the internal pressure between double membranes 10 and 11 presses reinforcing mushroom-shaped head 17 and jacket membrane 10 against the radial hole 12 to seal it against the escape of air.

It will be understood that during sexual intercourse, closure plug 9 is firmly placed within the basic body element 1 to form an effective contraceptive barrier. To urinate, the user can simply remove the closure plug 9 from the basic body element 1 and afterwards reinsert it.

To remove valve body 4 or 5 from the urethra, membrane 10, with its reinforcing mushroom-shaped head 17, is raised with the assistance of the small rod or plug 20 introduced into radial hole 12, so that the pressure fluid can escape from the space between double membrane tube 10, 11, through the plug 20 and to atmosphere through the camming sleeve 22. The device may then be removed from the urethra.

Of course, the entire valve body consists of material that is not irritating to the skin, and is biocompatible.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A removable closure device for a male urethra comprising:
   an elongated, cylindrical valve body having a longitudinally extending through bore extending between a forward open end and a rearward open end;
   a closure plug removably inserted in said forward open end;
   a double membrane sleeve telescopically received over said valve body and including an inner membrane and an outer membrane; and
   means for supplying fluid between said inner membrane and said outer membrane for expanding said outer membrane into sealing engagement with the urethra.

2. A closure device as defined in claim 1 wherein the removable plug includes pulling means for removing the plug.

3. A closure device as defined in claim 1 wherein said valve body is provided with a radial opening extending between said through bore and said double membrane sleeve.

4. A closure device as defined in claim 3 wherein a fluid passage is provided in said inner membrane to operatively connect said through bore to a space between said inner and outer membranes.

5. A closure device as defined in claim 4 wherein said means for supplying fluid is operative to pass fluid through said forward open end, said through bore, said radial opening and said fluid passage.

6. A closure device as defined in claim 5 wherein a reinforcing member is fastened to said inner membrane adjacent said radial opening so that, when said outer membrane is expanded, the radial opening is sealed shut by said reinforcing member and said inner membrane.

7. A closure device as defined in claim 1 wherein said elongated valve body comprises a body element, an intermediate element and an end element, and further wherein said body element, said intermediate element and said end element are flexibly attached in end-to-end relationship.

8. A closure device as defined in claim 7 wherein said inner membrane encloses each of said body element, said intermediate element and said end element, and wherein said outer membrane encloses at least said valve body element.

9. A closure device as defined in claim 7 wherein the forward open end of the valve body element has a smooth rounded surface which lies flush with said closure plug.

10. A closure device as defined in claim 7 wherein said valve body element is provided with a radial opening extending between said through bore and said double membrane sleeve 11. A closure device as defined in claim 10 wherein a fluid passage is provided in said inner membrane to operatively connect said through bore to a space between said inner and outer membranes.

12. A closure device as defined in claim 11 wherein said means for supplying fluid is operative to pass fluid through said forward open end, said through bore, said radial opening and said fluid passage.

13. A closure device as defined in claim 12 wherein a reinforcing member is fastened to said inner membrane adjacent said radial opening so that, when said outer membrane is expanded, the radial opening is sealed shut by said reinforcing member and said inner membrane.

14. A closure device for a male urethra comprising an elongated valve body adapted to be inserted in the urethra and removably secured therein in airtight and liquid-tight relationship therewith, said valve body including flexibly interconnected, substantially cylindrical forward, intermediate and end elements, wherein at least said forward element is provided with radially expandable means telescopically received over said valve body for securing the valve body in the urethra; said valve body having an open forward end and an open rearward end connected by a longitudinal through bore; and a plug removably inserted in said open end.

15. A closure device as defined in claim 14 wherein said forward, intermediate and end elements are telescopically interconnected and include cooperable tapered boss and groove means for retaining said elements in flexible interconnected relationship.

16. A closure device as defined in claim 15 wherein said through bore extending through said elements is coated at least in areas adjacent the interconnection of said elements.

17. A closure device as defined in claim 14 wherein a sleeve is fitted within said open end, and said removable plug is friction fit within said sleeve.

18. A closure device as defined in claim 14 wherein all of said elements have substantially identical outer diameters.

19. A closure device as defined in claim 14 wherein said radially expandable means includes at least one flexible membrane.

20. A closure device as defined in claim 19 wherein said at least one membrane is uniformly expandable along substantially the entire length thereof.

21. A closure device as defined in claim 19 wherein said at least one membrane is expandable in bellows form.

22. A closure device as defined in claim 19 wherein said radially expandable means includes an inner and outer membrane joined together to form a tube, wherein said inner membrane is provided with an air passage.

* * * * *